(12) United States Patent
Lin et al.

(10) Patent No.: US 7,556,784 B2
(45) Date of Patent: Jul. 7, 2009

(54) OPTIMIZED PRODUCTION OF AROMATIC DICARBOXYLIC ACIDS

(75) Inventors: Robert Lin, Kingsport, TN (US); Marcel de Vreede, Barendrecht (NL)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 12/050,251

(22) Filed: Mar. 18, 2008

(65) Prior Publication Data

US 2008/0159929 A1 Jul. 3, 2008

Related U.S. Application Data

(62) Division of application No. 11/181,214, filed on Jul. 14, 2005.

(60) Provisional application No. 60/606,807, filed on Sep. 2, 2004.

(51) Int. Cl.
*B01J 10/00* (2006.01)
*B01J 8/04* (2006.01)
*C07C 51/255* (2006.01)
*C07C 51/42* (2006.01)

(52) U.S. Cl. .................. 422/189; 422/193; 422/226; 422/235; 422/282; 562/412; 562/414; 562/416; 562/487; 562/531

(58) Field of Classification Search .............. 422/189, 422/226, 234, 245.1, 193, 235; 562/412, 562/414, 416, 418, 486, 487, 531
See application file for complete search history.

(56) References Cited

U.S. PATENT DOCUMENTS

| | | | |
|---|---|---|---|
| 2,964,559 A | 12/1960 | Burney et al. | |
| 3,170,768 A * | 2/1965 | Baldwin | 422/189 |
| 3,840,641 A | 10/1974 | Wampfler et al. | |
| 3,873,468 A | 3/1975 | Kobinata et al. | |
| 3,950,409 A | 4/1976 | Yokota et al. | |
| 3,996,271 A | 12/1976 | Yokota et al. | |
| 4,081,464 A | 3/1978 | Marsh et al. | |
| 4,158,738 A | 6/1979 | Scott et al. | |
| 4,185,073 A | 1/1980 | Marsh et al. | |
| 4,219,669 A | 8/1980 | Tsuchiya et al. | |
| 4,298,580 A | 11/1981 | Harper et al. | |
| 4,330,676 A | 5/1982 | Moxham | |
| 4,356,319 A | 10/1982 | Roffia et al. | |

(Continued)

FOREIGN PATENT DOCUMENTS

DE 2131470 A 6/1970

(Continued)

OTHER PUBLICATIONS

USPTO Office Action dated Mar. 6, 2009 for copending U.S. Appl. No. 11/655,395.

(Continued)

*Primary Examiner*—Walter D Griffin
*Assistant Examiner*—Huy-Tram Nguyen
(74) *Attorney, Agent, or Firm*—Bernard J. Graves, Jr.; Steven A. Owen

(57) ABSTRACT

Disclosed is an optimized process and apparatus for more efficiently and economically producing aromatic discarboxylic acids. The process reduces costs associated with hydrogenation by forming a final composite product containing unhydrogenated acid particles.

25 Claims, 1 Drawing Sheet

U.S. PATENT DOCUMENTS

| | | | |
|---|---|---|---|
| 4,769,489 A | 9/1988 | Abrams et al. | |
| 4,892,972 A * | 1/1990 | Schroeder et al. | 562/487 |
| 4,914,230 A | 4/1990 | Abrams et al. | |
| 4,939,297 A | 7/1990 | Browder et al. | |
| 5,110,984 A * | 5/1992 | Janulis | 562/487 |
| 5,200,557 A | 4/1993 | Gee et al. | |
| 5,201,940 A * | 4/1993 | Batterham et al. | 75/414 |
| 5,643,468 A | 7/1997 | Ure | |
| 5,676,847 A | 10/1997 | Yamamoto et al. | |
| 5,705,682 A | 1/1998 | Ohkashi et al. | |
| 5,770,765 A | 6/1998 | Ohkoshi | |
| 5,840,965 A | 11/1998 | Turner et al. | |
| 5,916,422 A | 6/1999 | Kimura et al. | |
| 5,955,394 A | 9/1999 | Kelly | |
| 5,973,196 A * | 10/1999 | Takano et al. | 562/485 |
| 5,994,567 A * | 11/1999 | Kingsley et al. | 552/208 |
| 6,054,610 A | 4/2000 | Lee et al. | |
| 6,133,476 A | 10/2000 | Lin | |
| 6,143,925 A * | 11/2000 | Tomitaka et al. | 562/412 |
| 6,153,790 A | 11/2000 | June et al. | |
| 6,362,367 B2 * | 3/2002 | Braithwaite et al. | 562/531 |
| 6,562,997 B2 | 5/2003 | Sikkenga et al. | |
| 7,074,954 B2 | 7/2006 | Sheppard et al. | |
| 7,132,566 B2 | 11/2006 | Sumner et al. | |
| 2001/0001649 A1* | 5/2001 | Decoster et al. | 422/189 |
| 2001/0041811 A1 | 11/2001 | Sikkenga et al. | |
| 2002/0016500 A1 | 2/2002 | Matsumoto et al. | |
| 2002/0193630 A1* | 12/2002 | Lin et al. | 562/414 |
| 2004/0225148 A1 | 11/2004 | Isogai et al. | |
| 2004/0244536 A1 | 12/2004 | Lin | |
| 2004/0245176 A1 | 12/2004 | Parker et al. | |
| 2004/0249207 A1 | 12/2004 | Lin et al. | |
| 2004/0249208 A1 | 12/2004 | Lin et al. | |
| 2007/0205153 A1 | 9/2007 | Parker et al. | |
| 2007/0208195 A1 | 9/2007 | Gibson et al. | |
| 2007/0208196 A1 | 9/2007 | Parker et al. | |
| 2007/0208197 A1 | 9/2007 | Gibson et al. | |
| 2007/0208198 A1 | 9/2007 | Parker et al. | |
| 2007/0208199 A1 | 9/2007 | Parker et al. | |
| 2007/0213557 A1 | 9/2007 | Seiki et al. | |
| 2008/0103333 A1 | 5/2008 | Nubel et al. | |

FOREIGN PATENT DOCUMENTS

| | | |
|---|---|---|
| EP | 0 181 127 A2 | 5/1986 |
| EP | 0 764 627 A1 | 3/1997 |
| EP | 0 579 715 B1 | 8/1997 |
| EP | 1 484 305 A1 | 8/2004 |
| EP | 1 484 306 A1 | 8/2004 |
| GB | 892766 A | 3/1962 |
| GB | 1407705 | 9/1975 |
| GB | 2067563 A | 7/1981 |
| JP | 46-14339 B | 11/1974 |
| JP | 51-145488 A | 12/1976 |
| JP | 49-123191 A | 2/1979 |
| JP | 54-25292 A | 2/1979 |
| JP | 62-25651 B2 | 6/1987 |
| JP | 09-048744 A | 2/1997 |
| JP | 9-157214 A | 6/1997 |
| JP | 10-114699 A | 5/1998 |
| JP | 11-349529 A | 12/1999 |
| JP | 3211396 B2 | 9/2001 |
| JP | 3232678 B2 | 11/2001 |
| JP | 59-53441 A | 3/2004 |
| WO | WO 92/18453 | 10/1992 |
| WO | WO 92/18454 A1 | 10/1992 |
| WO | WO 93/24441 A | 12/1993 |
| WO | WO 97/27168 A1 | 7/1997 |
| WO | WO 97/30963 A | 8/1997 |
| WO | WO 00/31014 A1 | 6/2000 |
| WO | WO 01/55075 A2 | 8/2001 |

OTHER PUBLICATIONS

BHS—Werk Sonthofen, *BHS-FEST Pressure Filter*, 1990, pamphlet, Santhofen, West Germany.

USPTO Office Action dated Oct. 20, 2004 for U.S. Appl. No. 10/455,017.

USPTO Office Action dated Jun. 6, 2005 for U.S. Appl. No. 10/455,017.

USPTO Office Action dated Nov. 10, 2005 for U.S. Appl. No. 10/455,017.

USPTO office action dated Jul. 19, 2006 for copending U.S. Appl. No. 10/455,017.

USPTO office action dated Jul. 19, 2006 for copending U.S. Appl. No. 10/455,018.

USPTO office action dated Dec. 27, 2006 for copending U.S. Appl. No. 10/455,018.

USPTO office action dated Jul. 19, 2006 for copending U.S. Appl. No. 10/455,016.

USPTO office action dated Jan. 18, 2007 for copending U.S. Appl. No. 10/455,017.

USPTO office action dated May 11, 2007 for copending U.S. Appl. No. 10/455,017.

USPTO office action dated Sep. 11, 2007 for copending U.S. Appl. No. 10/455,017.

USPTO office action dated May 14, 2007 for copending U.S. Appl. No. 10/455,018.

USPTO Notice of Allowance dated Sep. 11, 2007 for copending U.S. Appl. No. 10/455,018.

USPTO Office Action dated May 17, 2007 for copending U.S. Appl. No. 11/201,512.

USPTO Office Action dated Jul. 6, 2007 for copending U.S. Appl. No. 11/455,016.

Treybal, Robert E., "Stagewise Contact, Single-Stage Extraction," Mass-Transfer Operations, Third Edition, 1980, pp. 490-555, McGraw-Hill Book Company.

Copending application U.S. Appl. No. 10/455,016, filed Jun. 5, 2003, Robert Lin.

Copending U.S. Appl. No. 10/455,017, filed Jun. 5, 2003, Robert Lin et al.

Copending U.S. Appl. No. 10/455,018, filed Jun. 5, 2003, Robert Lin et al.

Copending U.S. Appl. No. 10/948,591, filed Sep. 24, 2004, Robert Lin et al.

Copending U.S. Appl. No. 10/948,678, filed Sep. 24, 2004, Robert Lin et al.

Copending U.S. Appl. No. 11/181,214, filed Jul. 14, 2005, Robert Lin et al.

Copending U.S. Appl. No. 11/181,449, filed Jul. 14, 2005, Robert Lin et al.

Copending U.S. Appl. No. 11/201,512, filed Aug. 11, 2005, Robert Lin et al.

Copending U.S. Appl. No. 11/201,799, filed Aug. 11, 2005, Robert Lin et al.

Copending U.S. Appl. No. 11/655,395, filed Jan. 19, 2007, Philip E. Gibson et al.

Copending U.S. Appl. No. 11/839,575, filed Aug. 16, 2007, Philip E. Gibson et al.

Copending U.S. Appl. No. 11/655,317, filed Jan. 19, 2007, Philip E. Gibson et al.

Copending U.S. Appl. No. 11/839,578, filed Aug. 16, 2007, Philip E. Gibson et al.

Copending U.S. Appl. No. 11/839,582, filed Aug. 16, 2007, Philip E. Gibson et al.

Copending U.S. Appl. No. 11/655,396, filed Jan. 19, 2007, Kenny R. Parker et al.

Copending U.S. Appl. No. 11/839,573, filed Aug. 16, 2007, Kenny R. Parker et al.

Copending U.S. Appl. No. 11/842,469, filed Aug. 21, 2007, Kenny Randolph Parker, et al.

USPTO Office Action dated Sep. 25, 2007 for copending U.S. Appl. No. 11/655,396.

USPTO Office Action dated Sep. 25, 2007 for copending U.S. Appl. No. 11/655,395.
USPTO Notice of Allowance dated Dec. 3, 2007 for copending U.S. Appl. No. 10/455,017.
USPTO Notice of Allowance dated Jan. 15, 2008 for copending U.S. Appl. No. 10/455,016.
USPTO Office Action dated Feb. 14, 2008 for copending U.S. Appl. No. 11/842,469.
USPTO Office Action dated Mar. 12, 2009 for copending U.S. Appl. No. 12/050,256.
USPTO Office Action dated Mar. 13, 2009 for copending U.S. Appl. No. 12/050,253.
USPTO Office Action dated Mar. 4, 2008 for copending U.S. Appl. No. 11/839,575.
USPTO Office Action dated Mar. 5, 2008 for copending U.S. Appl. No. 11/655,317.
USPTO Office Action dated Mar. 4, 2008 for copending U.S. Appl. No. 11/839,578.
USPTO office Action dated Mar. 5, 2008 for copending U.S. Appl. No. 11/655,396.
USPTO Office Action dated Mar. 7, 2008 for copending U.S. Appl. No. 10/948,591.
USPTO Office Action dated Mar. 14, 2008 for copending U.S. Appl. No. 10/948,678.
USPTO Office Action dated Mar. 11, 2008 for copending U.S. Appl. No. 11/655,395.
USPTO Office Action dated Mar. 11, 2008 for copending U.S. Appl. No. 11/839,582.
USPTO Office Action dated Mar. 11, 2008 for copending U.S. Appl. No. 11/839,573.
Copending U.S. Appl. No. 12/050,258, filed Mar. 18, 2008, Robert Lin et al.
Copending U.S. Appl. No. 12/050,253, filed Mar. 18, 2008, Robert Lin et al.
Copending U.S. Appl. No. 12/050,256, filed Mar. 18, 2008, Robert Lin et al.
USPTO Office Action dated Apr. 4, 2008 for copending U.S. Appl. No. 11/181,449.
USPTO Office Action dated Apr. 13, 2009 for copending U.S. Appl. No. 11/181,449.
USPTO Office Action dated Apr. 25, 2008 for copending U.S. Appl. No. 11/181,214.
USPTO Notice of Allowance dated Oct. 1, 2008 for copending U.S. Appl. No. 10/948,591.
USPTO Notice of Allowance dated Oct. 10, 2008 for copending U.S. Appl. No. 11/842,469.
USPTO Office Action dated Oct. 28, 2008 for copending U.S. Appl. No. 11/181,449.
USPTO Office Action dated Nov. 5, 2008 for copending U.S. Appl. No. 11/201,799.
USPTO Notice of Allowance dated Nov. 12, 2008 for copending U.S. Appl. No. 10/948,678.
USPTO Office Action dated Nov. 14, 2008 for copending U.S. Appl. No. 11/655,317.
USPTO Office Action dated Dec. 5, 2008 for copending U.S. Appl. No. 11/655,396.
USPTO Office Action dated Dec. 11, 2008 for copending U.S. Appl. No. 11/839,575.
USPTO Office Action dated Dec. 10, 2008 for copending U.S. Appl. No. 11/839,578.
USPTO Office Action dated Dec. 10, 2008 for copending U.S. Appl. No. 11/839,582.
USPTO Office Action dated Dec. 11, 2008 for copending U.S. Appl. No. 11/839,573.
USPTO Office Action dated May 21, 2009 for copending U.S. Appl. No. 11/181,214.

* cited by examiner

US 7,556,784 B2

OPTIMIZED PRODUCTION OF AROMATIC DICARBOXYLIC ACIDS

CROSS-REFERENCE TO RELATED APPLICATIONS

This application is a divisional of application Ser. No. 11/181,214, entitled "Optimized Production of Aromatic Dicarboxylic Acids," filed on Jul. 14, 2005, which claims priority to U.S. Provisional Application Ser. No. 60/606,807, filed Sep. 2, 2004, the disclosures of which are incorporated herein by reference in their entirety to the extent they do not contradict statements herein.

FIELD OF THE INVENTION

This invention relates generally to the production of aromatic dicarboxylic acids, such as terephthalic acid. One aspect of the invention concerns a more efficient method of producing aromatic dicarboxylic acids. Another aspect of the invention concerns a method for controlling the purity of an aromatic dicarboxylic acid product.

BACKGROUND OF THE INVENTION

Terephthalic acid (TPA) is one of the basic building blocks in the production of linear polyester resins used in the manufacture of polyester films, packaging materials, and bottles. TPA used in the manufacture of such polyesters resins must meet certain minimum purity requirements.

The purified condition of TPA refers primarily to the absence of significant concentrations of 4-carboxybenzaldehyde (4-CBA) and para-toluic acid (p-TAc) that are present in significant quantities in the commercially-available crude grades of TPA. Both 4-CBA and p-TAc are partial oxidation products formed in the manufacture of TPA by the catalytic oxidation of para-xylene. The purified form of TPA also refers to the absence of color bodies that impart a characteristic yellow hue to the crude material. The color bodies are aromatic compounds having the structures of benzils, fluorenones, and/or anthraquinones. 4-CBA and p-TAc are particularly detrimental to the polymerization process as they act as chain terminators during the condensation reaction between TPA and ethylene glycol in the production of polyethylene terephthalate (PET).

To obtain purified terephthalic acid (PTA) from crude terephthalic acid (CTA), the 4-CBA and the color bodies can be hydrogenated, the 4-CBA to p-TAc and the color bodies to colorless solid compounds. To accomplish this purification, the solid CTA particles are typically dissolved in a solvent (e.g., water), and the resulting solution is subjected to liquid-phase hydrogenation in the presence of a hydrogenation catalyst. Although effective to reduce yellowness, purification of CTA by hydrogenation can be expensive because it consumes energy, hydrogen, water, and catalyst. Hence, from the standpoint of operational cost, it would be desirable to minimize the amount of hydrogenation required to produce TPA solids of suitable purity.

SUMMARY OF THE INVENTION

One embodiment of the present invention provides a process comprising: (a) providing a quantity of crude acid particles; (b) subject a first portion of the crude acid particles to hydrogenation treatment to thereby produce a hydrogenation-treated acid; and (c) combining a second portion of the crude acid particles that has not been subjected to hydrogenation treatment with at least a portion of the hydrogenation-treated acid, thereby producing a composite acid.

Another embodiment of the invention provides an apparatus comprising an oxidation reactor, a solid/liquid separator, a splitter, a hydrogenation system, and a combining zone. The oxidation reactor has an outlet that is coupled in communication with an inlet of the separator. The separator has a separated solids outlet and a separated liquids outlet. The separated solids outlet is coupled in communication with an inlet of the splitter. The splitter has first and second outlets. The first outlet of the splitter is coupled in communication with an inlet of the hydrogenation system. The combining zone has a hydrogenated solids inlet, an unhydrogenated solids inlet, and a composite solids outlet. The second outlet of the splitter is coupled in communication with the unhydrogenated solids inlet of the combining zone. The hydrogenation system has an outlet that is coupled in communication with the hydrogenated solids inlet of the combining zone.

DETAILED DESCRIPTION

Figure 1:
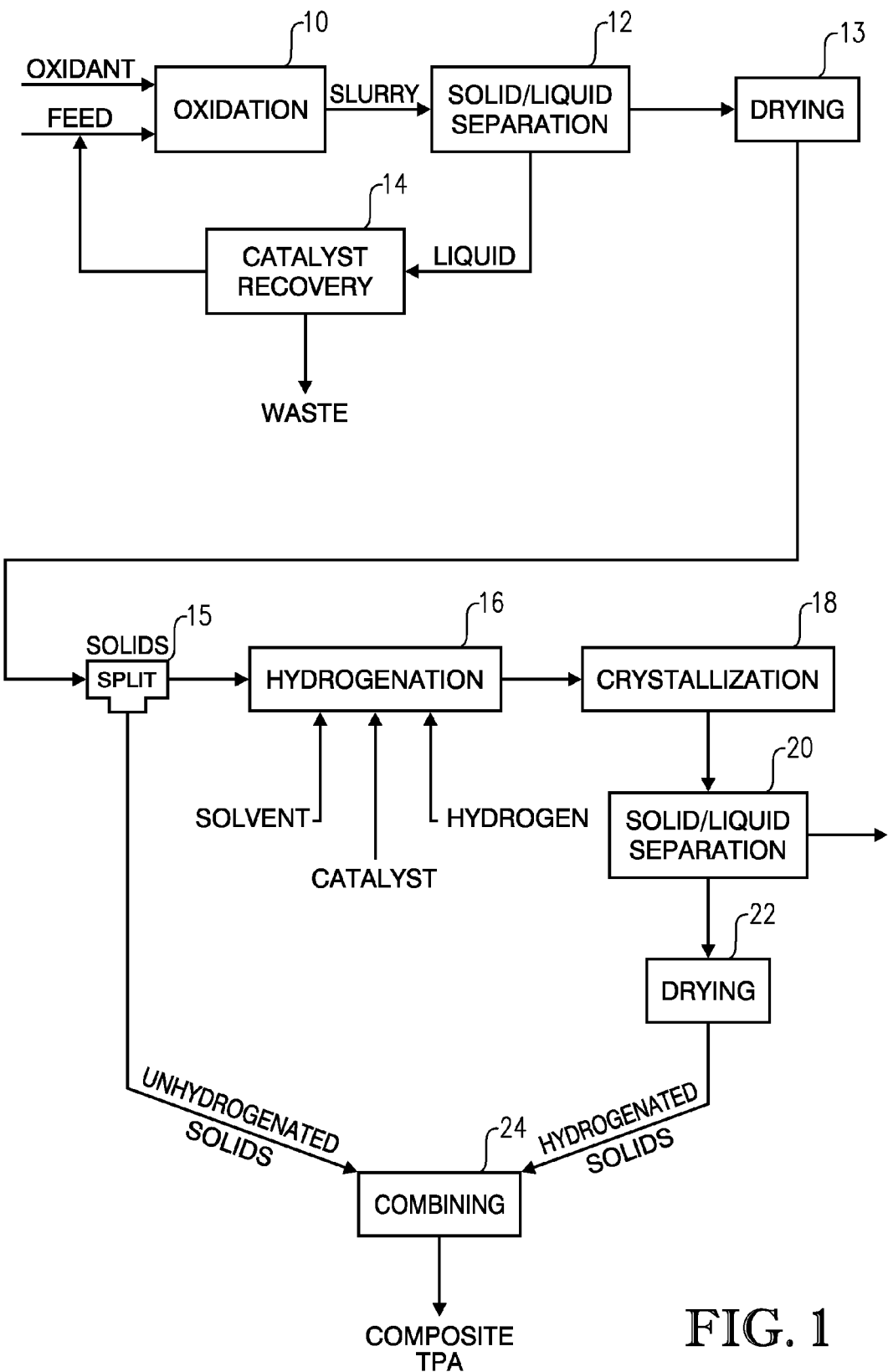
FIG. 1 is a process flow diagram illustrating a system for the production of a composite terephthalic acid formed by combining a quantity of purified/hydrogenated terephthalic acid with a quantity of crude/unhydrogenated terephthalic acid.

Crude aromatic dicarboxylic acids, such as crude terephthalic acid (CTA), may be produced and purified using the inventive system illustrated in FIG. 1. As shown in FIG. 1, in a first step of the process, a predominately liquid-phase feed stream containing an oxidizable compound (e.g., para-xylene), a solvent (e.g., acetic acid+water), and a catalyst system (e.g., Co+Mn+Br) is introduced into an oxidation reactor 10. A predominately gas-phase oxidant stream containing molecular oxygen is also introduced into reactor 10. The liquid- and gas-phase feed streams form a multi-phase reaction medium in reactor 10. The oxidizable compound undergoes partial oxidation in a liquid phase of the reaction medium contained in reactor 10.

Oxidation reactor 10 is preferably an agitated reactor. Agitation of the reaction medium in oxidation reactor 10 can be provided by any means known in the art. As used herein, the term "agitation" shall denote work dissipated into the reaction medium causing fluid flow and/or mixing. In one embodiment, oxidation reactor 10 is a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In another embodiment of the invention, oxidation reactor 10 is a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the terms "majority," "primarily," and "predominately" shall mean more than 50 percent.

The oxidizable compound present in the liquid-phase feed stream introduced into oxidation reactor 10 preferably comprises at least one hydrocarbyl group. More preferably, the oxidizable compound is an aromatic compound. Still more preferably, the oxidizable compound is an aromatic compound with at least one attached hydrocarbyl group or at least one attached substituted hydrocarbyl group or at least one attached heteroatom or at least one attached carboxylic acid function (—COOH). Even more preferably, the oxidizable compound is an aromatic compound with at least one attached hydrocarbyl group or at least one attached substituted hydrocarbyl group with each attached group comprising from 1 to 5 carbon atoms. Yet still more preferably, the oxidizable compound is an aromatic compound having exactly two attached groups with each attached group comprising exactly one carbon atom and consisting of methyl groups and/or substituted methyl groups and/or at most one carboxylic acid group. Even still more preferably, the oxidizable compound is para-xylene, meta-xylene, para-tolualdehyde, meta-tolualdehyde, para-toluic acid, meta-toluic acid, and/or acetaldehyde. Most preferably, the oxidizable compound is para-xylene.

A "hydrocarbyl group," as defined herein, is at least one carbon atom that is bonded only to hydrogen atoms or to other carbon atoms. A "substituted hydrocarbyl group", as defined herein, is at least one carbon atom bonded to at least one heteroatom and to at least one hydrogen atom. "Heteroatoms," as defined herein, are all atoms other than carbon and hydrogen atoms. Aromatic compounds, as defined herein, comprise an aromatic ring, preferably having at least 6 carbon atoms, even more preferably having only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the liquid-phase feed stream introduced into oxidation reactor 10 is preferably in the range of from about 2 to about 40 weight percent, more preferably in the range of from about 4 to about 20 weight percent, and most preferably in the range of from 6 to 15 weight percent.

The solvent present in the liquid-phase feed stream introduced into oxidation reactor 10 preferably comprises an acid component and a water component. The solvent is preferably present in the liquid-phase feed stream at a concentration in the range of from about 60 to about 98 weight percent, more preferably in the range of from about 80 to about 96 weight percent, and most preferably in the range of from 85 to 94 weight percent. The acid component of the solvent is preferably an organic low molecular weight monocarboxylic acid having 1-6 carbon atoms, more preferably 2 carbon atoms. Most preferably, the acid component of the solvent is acetic acid. Preferably, the acid component makes up at least about 75 weight percent of the solvent, more preferably at least about 80 weight percent of the solvent, and most preferably 85 to 98 weight percent of the solvent, with the balance being water.

The liquid-phase feed stream introduced into oxidation reactor 10 can also include a catalyst system. The catalyst system is preferably a homogeneous, liquid-phase catalyst system capable of promoting partial oxidation of the oxidizable compound. More preferably, the catalyst system comprises at least one multivalent transition metal. Still more preferably, the multivalent transition metal comprises cobalt. Even more preferably, the catalyst system comprises cobalt and bromine. Most preferably, the catalyst system comprises cobalt, bromine, and manganese.

When cobalt is present in the catalyst system, it is preferred for the amount of cobalt present in the liquid-phase feed stream to be such that the concentration of cobalt in the liquid phase of the reaction medium is maintained in the range of from about 300 to about 6,000 parts per million by weight (ppmw), more preferably in the range of from about 700 to about 4,200 ppmw, and most preferably in the range of from 1,200 to 3,000 ppmw. When bromine is present in the catalyst system, it is preferred for the amount of bromine present in the liquid-phase feed stream to be such that the concentration of bromine in the liquid phase of the reaction medium is maintained in the range of from about 300 to about 5,000 ppmw, more preferably in the range of from about 600 to about 4,000 ppmw, and most preferably in the range of from 900 to 3,000 ppmw. When manganese is present in the catalyst system, it is preferred for the amount of manganese present in the liquid-phase feed stream to be such that the concentration of manganese in the liquid phase of the reaction medium is maintained in the range of from about 20 to about 1,000 ppmw, more preferably in the range of from about 40 to about 500 ppmw, most preferably in the range of from 50 to 200 ppmw.

The weight ratio of cobalt to bromine (Co:Br) in the catalyst system introduced into oxidation reactor 10 is preferably in the range of from about 0.25:1 to about 4:1, more preferably in the range of from about 0.5:1 to about 3:1, and most preferably in the range of from 0.75:1 to 2:1. The weight ratio of cobalt to manganese (Co:Mn) in the catalyst system introduced is preferably in the range of from about 0.3:1 to about 40:1, more preferably in the range of from about 5:1 to about 30:1, and most preferably in the range of from 10:1 to 25:1.

During oxidation, it is preferred for the oxidizable compound (e.g., para-xylene) to be continuously introduced into oxidation reactor 10 at a rate of at least about 5,000 kilograms per hour, more preferably at a rate in the range of from about 10,000 to about 80,000 kilograms per hour, and most preferably in the range of from 20,000 to 50,000 kilograms per hour. During oxidation, it is preferred for the ratio of the mass flow rate of the solvent to the mass flow rate of the oxidizable compound entering oxidation reactor 10 to be maintained in the range of from about 2:1 to about 50:1, more preferably in the range of from about 5:1 to about 40:1, and most preferably in the range of from 7.5:1 to 25:1.

The predominately gas-phase oxidant stream introduced into oxidation reactor 10 preferably comprises in the range of from about 5 to about 40 mole percent molecular oxygen, more preferably in the range of from about 15 to about 30 mole percent molecular oxygen, and most preferably in the range of from 18 to 24 mole percent molecular oxygen. It is preferred for the balance of the oxidant stream to be comprised primarily of a gas or gases, such as nitrogen, that are inert to oxidation. More preferably, the oxidant stream consists essentially of molecular oxygen and nitrogen. Most preferably, the oxidant stream is dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in oxidation reactor 10, it is preferred for the oxidant stream to be introduced into reactor 10 in an amount that provides molecular oxygen somewhat exceeding the stoichiometric oxygen demand. Thus, it is preferred that the ratio of the mass flow rate of the oxidant stream (e.g., air) to the mass flow rate of the oxidizable compound (e.g., para-xylene) entering reactor 10 is maintained in the range of from about 0.5:1 to about 20:1, more preferably in the range of from about 1:1 to about 10:1, and most preferably in the range of from 2:1 to 6:1.

The liquid-phase oxidation reaction carried out in reactor 10 is preferably a precipitating reaction that generates solids. More preferably, the liquid-phase oxidation carried out in reactor 10 causes at least about 10 weight percent of the oxidizable compound (e.g., para-xylene) introduced into oxidation reactor 10 to form solids (e.g., CTA particles) in the reaction medium. Still more preferably, the liquid-phase oxidation causes at least about 50 weight percent of the oxidizable compound to form solids in the reaction medium. Most preferably, the liquid-phase oxidation causes at least 90 weight percent of the oxidizable compound to form solids in the reaction medium. It is preferred that the total amount of solids in the reaction medium is maintained in the range of from about 5 to about 40 weight percent, still more preferably in the range of from about 10 to about 35 weight percent, and most preferably in the range of from 15 to 30 weight percent.

During oxidation in oxidation reactor 10, the multi-phase reaction medium is preferably maintained at an elevated temperature in the range of from about 140 to about 300° C., more preferably in the range of from about 175 to about 250° C., and most preferably in the range of from 190 to 225° C. The overhead pressure in oxidation reactor 10 is preferably maintained in the range of from about 1 to about 20 bar guage (barg), more preferably in the range of from about 2 to about 12 barg, and most preferably in the range of from 4 to 8 barg.

As illustrated in FIG. 1, a slurry containing solid particles of the crude oxidation product (e.g., CTA) is withdrawn from an outlet of oxidation reactor 10. The solids content of the withdrawn slurry is preferably in the range described above with reference to the solids content of the reaction medium in reactor 10. The withdrawn slurry from reactor 10 is introduced into a solid/liquid separator 12 where the slurry is subjected to solid/liquid separation. Separator 12 can be any conventional solid/liquid separation means including, for example, a decanter centrifuge, a rotary disk centrifuge, a belt filter, or a rotary vacuum filter.

The liquid "mother liquor" discharged through a liquids outlet of solid/liquid separator 12 is introduced into a catalyst recovery system 14. The liquid mother liquor is typically comprised mostly of the solvent and the catalyst system; however, the mother liquor may also contain undesirable corrosion/tramp metals such as iron, nickel and chromium, as well as undesired organic reaction products which have built up over time. Catalyst recovery system 14 employs a conventional method to remove a substantial portion of the undesirable components present in the liquid mother liquor. As illustrated in FIG. 1, the resulting cleaned liquid stream can be combined with the liquid-phase feed stream introduced into oxidation reactor 10.

The crude acid solids (e.g., CTA) discharged through a solids outlet of solid/liquid separator 12 typically is in the form of a solvent wet cake. Optionally, one or more dryers 13 can be utilized to evaporate residual solvent. The CTA has a 4-CBA content greater than about 600 parts per million by weight (ppmw). More typically, the 4-CBA content of the crude acid solids is in the range of from about 700 to about 10,000 ppmw, and most typically in the range of from 800 to 7,000 ppmw. Typically, the crude acid solids have a p-TAc content greater than about 150 ppmw. More typically, the p-TAc content of the crude acid solids is in the range of from about 175 to about 5,000 ppmw, and most typically in the range of from 200 to 1,500 ppmw. Typically, the crude acid solids have a combined 4-CBA plus p-TAc content greater than about 700 ppmw. More typically, the combined 4-CBA and p-TAc content of the crude acid solids is in the range of from about 850 to about 5,000 ppmw, and most typically in the range of from 1,000 to 10,000 ppmw. Typically, the crude acid solids have a B* value of at least 3, more typically in the range of from about 3.5 to about 10, and most typically 4 to 8.

Referring again to FIG. 1, the crude acid solids (e.g., CTA) discharged from solid/liquid separator 12 are introduced into a splitter 15 where the solids are divided into a first portion and a second portion. Splitter 15 can be any conventional means for separating solids. The first portion of the crude acid solids exits a first outlet of splitter 15 and is subsequently subjected to purification in a hydrogenation system 16. The second portion of the crude acid solids exits a second outlet of splitter 15 and is not subject to hydrogenation treatment. It is preferred for at least about 1 weight percent of the crude acid solids (e.g., CTA) produced in oxidation reactor 10 to exit the second outlet of splitter 15 and not be subjected to hydrogenation treatment, more preferably in the range of from about 3 to about 60 weight percent of the crude acid solids are not subjected to hydrogenation treatment, and most preferably in the range of from 5 to about 40 weight percent of the crude acid solids are not subjected to hydrogenation treatment. In addition, it is preferred for the weight ratio of the second portion of the crude acid solids (not subjected to hydrogenation) to the first portion of the crude acid solids (subsequently subjected to hydrogenation) to be in the range of from about 0.01:1 to about 4:1, more preferably in the range of from about 0.05:1 to about 2:1, and most preferably in the range of from 0.1:1 to 1:1.

Hydrogenation system 16 receives the first portion of the crude acid solids from splitter 15. Hydrogenation system 16 can include one or more vessels/zones. Preferably, hydrogenation system 16 includes an initial dissolution zone/vessel where the crude acid solids (e.g., CTA) are combined with a solvent (preferably water) at an elevated temperature to thereby cause dissolution of the crude acid solids in the solvent. The solvent and crude acid particles are preferably combined at a solvent-to-crude acid weight ratio in the range of from about 0.5:1 to about 50:1, more preferably in the range of from about 1:1 to about 10:1, and most preferably in the range of from 1.5:1 to 5:1.

After dissolution of the crude acid particles in the solvent, the resulting solution is introduced into a hydrogenation zone/vessel of hydrogenation system 16 where the solution is contacted with hydrogen and a hydrogenation catalyst under conditions sufficient to cause hydrogenation of certain impurities present therein (e.g., hydrogenation of 4-CBA to p-TAc and/or floureneones to flourenes). In a preferred embodiment of the invention, hydrogenation treatment is carried out at a temperature in the range of from about 200 to about 375° C., more preferably in the range of from about 225 to about 300° C., and most preferably in the range of from 240 to 280° C. The pressure in the hydrogenation zone/vessel is preferably maintained in the range of from about 2 to about 50 barg. The average space velocity for hydrogenation is preferably maintained in the range of from about 150 to about 2,500 kilograms of solution per hour per cubic meter of catalyst bed (kg/hr/m$^3$), more preferably in the range of from about 300 to about 1,500 kg/hr/m$^3$, and most preferably in the range of from 450 to 850 kg/hr/m$^3$. The molar ratio of hydrogen fed to the hydrogenation zone/vessel to crude acid fed to the hydrogenation zone/vessel is preferably in the range of from about 5:1 to about 500:1, more preferably in the range of from about 10:1 to about 300:1, and most preferably in the range of from 20:1 to 250:1. The hydrogenation catalyst employed in the hydrogenation zone/vessel is preferably a noble Group VIII metal on a conventional catalyst support material.

After hydrogenation treatment in hydrogenation system 16, the resulting hydrogenation-treated solution is subjection to crystallization in a crystallization system 18 comprising at least one crystallizer. In crystallization system 18, the temperature of the hydrogenated solution is lowered to a crystallization temperature in the range of from about 100 to about 200° C., more preferably in the range of from about 120 to about 185° C., and most preferably in the range of from 140 to 175° C. The decreased temperature in crystallization system 18 causes substantially all of the aromatic dicarboxylic acid (e.g., TPA) dissolved in the hydrogenation-treated solution to crystallize, thereby forming solid particles of a purified/hydrogenated acid (e.g., PTA).

The two-phase (slurry) effluent from crystallization system 16 is thereafter subjected to solid/liquid separation in a conventional separator 20. The separated purified/hydrogenated acid solids (e.g., PTA) from separator 20 are then dried in one or more conventional driers 22.

The purified/hydrogenated acid solids (e.g., PTA) discharged from drier 22 preferably have a 4-CBA content less than or equal to 100 ppmw, more preferably less than 50 ppmw, and most preferably less than 25 ppmw. The purified acid solids preferably have a p-TAc content that is less than 500 ppmw, more preferably less than 250 ppmw, and most preferably less than 125 ppmw. The purified acid solids preferably have a B* value that is less than 3.0, more preferably less than 2.0, most preferably less than 1.5.

As illustrated in FIG. 1, at least a portion of purified/hydrogenated acid solids (e.g., PTA) exiting drier 22 are combined in a combining zone/vessel 24 with at least a portion of the crude/unhydrogenated acid solids (e.g., CTA) discharged from splitter 15. A composite acid (e.g., composite TPA) comprising the solid purified/hydrogenated acid particles and solid crude/unhydrogenated acid particles is produced in, and discharged from, mixing zone/vessel 24. The combining zone/vessel 24 can be any zone or vessel having an inlet for receiving the purified/hydrogenated acid, an inlet for receiving the crude/unhydrogenated acid, and an outlet for discharging the composite acid. The composite acid is just pure enough to meet product specifications, but not unnecessarily pure. Since not all of the acid of the final product has been subjected to hydrogenation treatment, various costs associated with hydrogenation are reduced, as compared to processes where all of the final acid product is previously subjected to hydrogenation treatment.

The specific amounts of purified/hydrogenated acid particles and crude/unhydrogenated acid particles combined in mixing zone/vessel 24 varies based on the level of impurities in the purified and crude acid particles, as well as the level of impurities permitted by the final product specifications. In a preferred embodiment of the present invention, the weight ratio of crude/unhydrogenated acid particles to purified/hydrogenated acid particles in the composite acid is in the range of from about 0.01:1 to about 4:1, more preferably in the range of from about 0.05:1 to about 2:1, and most preferably in the range of from about 0.1:1 to about 1:1.

The final composite acid (e.g., composite TPA) product exiting mixing zone/vessel 24 preferably has a 4-CBA content that is at least about 105 percent by weight of the 4-CBA content of the purified/hydrogenated acid (e.g., PTA) exiting drier 22, more preferably in the range of from about 110 to about 400 percent by weight, and most preferably in the range of from about 120 to about 200 percent by weight. The composite acid product preferably has a p-TAc content that is at least about 105 percent by weight of the p-TAc content of the purified/hydrogenated acid, more preferably in the range of from about 110 to about 400 percent by weight, and most preferably in the range of from about 120 to about 200 percent by weight. The composite acid product preferably has a combined 4-CBA plus p-TAc content that is at least about 105 percent by weight of the combined 4-CBA plus p-TAc content of the purified/hydrogenated acid, more preferably in the range of from about 110 to about 400 percent by weight, and most preferably in the range of from about 120 to about 200 percent by weight. The composite acid product preferably has a B* value that is at least about 105 percent of the B* value of the purified/hydrogenated acid, more preferably in the range of from about 110 to about 400, and most preferably in the range of from about 120 to about 200.

The inventors note that for all numerical ranges provided herein, the upper and lower ends of the ranges can be independent of one another. For example, a numerical range of 10 to 100 means greater than 10 and/or less than 100. Thus, a range of 10 to 100 provides support for a claim limitation of greater than 10 (without the upper bound), a claim limitation of less than 100 (without the lower bound), as well as the full 10 to 100 range (with both upper and lower bounds).

The inventors also note that, as used herein, "coupled in communication" denotes a direct or indirect connection that permits the flow of solids and/or liquids. For example, the outlet of oxidation reactor 10 (FIG. 1) is "coupled in communication" with the inlet of splitter 15, even though there is intermediate equipment (i.e., separator 12) located therebetween.

The invention has been described in detail with particular reference to preferred embodiments thereof, but will be understood that variations and modification can be affected within the spirit and scope of the invention.

We claim:

1. An apparatus comprising:
an oxidation reactor having a reactor outlet;
a solid/liquid separator having a separator inlet, a separated solids outlet, and a separated liquids outlet, wherein said separator inlet is coupled in communication with said reactor outlet;
a splitter having a splitter inlet, a first splitter outlet and a second splitter outlet, wherein said splitter inlet is coupled in communication with said separated solids;
a hydrogenation system having a hydrogenation system inlet and a hydrogenation system outlet, wherein said hydrogenation system inlet is coupled in communication with said first splitter outlet; and
a combining zone having a hydrogenated solids inlet, an unhydrogenated solids inlet, and a composite solids outlet, wherein said hydrogenated solids inlet is coupled in communication with said hydrogenation system outlet, wherein said unhydrogenated solids inlet is coupled in communication with said second splitter outlet.

2. The apparatus of claim 1 further comprising a crystallization system having a crystallization system inlet and a crystallization system outlet, wherein said crystallization inlet is coupled in communication with said hydrogenation system outlet, wherein said crystallization system inlet is coupled in communication with said hydrogenation system outlet.

3. The apparatus of claim 2 further comprising a second solid/liquid separator having a second separator inlet, a hydrogenated solids outlet, and hydrogenated liquids outlet, wherein said second separator inlet is coupled in communication with said crystallization system outlet, wherein said hydrogenated solids outlet is coupled in communication with said hydrogenated solids inlet.

4. The apparatus of claim 3 further comprising one or more hydrogenated solids dryers having a dryer inlet and a dryer outlet, wherein said dryer inlet is coupled in communication with said crystallization system outlet, wherein said dryer outlet is coupled in communication with said hydrogenated solids inlet.

5. The apparatus of claim 1 wherein said oxidation reactor is an agitated reactor.

6. The apparatus of claim 5 wherein said oxidation reactor is a mechanically-agitated reactor.

7. The apparatus of claim 5 wherein said oxidation reactor is a bubble column reactor.

8. The apparatus of claim 1 wherein said solid/liquid separator is selected from the group consisting of a decanter centrifuge, a rotary disk centrifuge, a belt filter, and a rotary filter.

9. The apparatus of claim 1 further comprising a catalyst recovery system having a recovery inlet and a recovery outlet, wherein said separated liquids outlet is coupled in communication with said recovery inlet.

10. The apparatus of claim 9 wherein said catalyst recovery system has a waste outlet and a clean liquid outlet, wherein said oxidation reactor has a feed inlet, wherein said clean liquid outlet is coupled in communication with said feed inlet.

11. The apparatus of claim 1 further comprising one or more dryers having a dryer inlet and a dryer outlet, wherein said dryer inlet is coupled in communication with said separated solids outlet, wherein said dryer outlet is coupled in communication with said splitter inlet.

12. The apparatus of claim 1 wherein no hydrogenation treatment system is disposed between said second splitter outlet and said unhydrogenated solids inlet.

13. The apparatus of claim 1 wherein said splitter is configured to receive solids in said splitter inlet and split said solids into a first portion exiting said first splitter outlet and a second portion exiting said second splitter outlet, wherein said splitter is configured to discharge from said second splitter outlet at least 1 weight percent of said solids received in said splitter inlet.

14. The apparatus of claim 13 wherein said splitter is configured to discharge from said second splitter outlet in the range of about 3 to about 60 weight percent of said unhydrogenated solids received in said splitter inlet.

15. The apparatus of claim 13 wherein said splitter is configured to discharge from said second splitter outlet in the range of 5 to 40 weight percent of said unhydrogenated solids received in said splitter inlet.

16. The apparatus of claim 1 wherein said splitter is configured to receive solids in said splitter inlet and split said solids into a first portion exiting said first splitter outlet and a second portion exiting said second splitter outlet, wherein said splitter is configured such that the weight ratio of solids exiting said second splitter outlet to solids exiting said first splitter outlet is in the range of about 0.01:1 to about 4:1.

17. The apparatus of claim 16 wherein said splitter is configured such that the weight ratio of solids exiting said second splitter outlet to solids exiting said first splitter outlet is in the range of about 0.05:1 to about 2:1.

18. The apparatus of claim 16 wherein said splitter is configured such that the weight ratio of unhydrogenated solids exiting said second splitter outlet to unhydrogenated solids exiting said first splitter outlet is in the range of 0.1:1 to 1:1.

19. The apparatus of claim 1 wherein said hydrogenation system comprises an initial dissolution vessel and a hydrogenation vessel.

20. The apparatus of claim 1 wherein said combining zone is configured to receive solids in said unhydrogenated solids inlet and to receive solids in said hydrogenated solids inlet, wherein the weight ratio of solids received in said unhydrogenated solids inlet to solids received in said hydrogenated solids inlet is in the range of about 0.01:1 to about 4:1.

21. The apparatus of claim 20 wherein the weight ratio of solids received in said unhydrogenated solids inlet to solids received in said hydrogenated solids inlet is in the range of about 0.05:1 to about 2:1.

22. The apparatus of claim 20 wherein the weight ratio of solids received in said unhydrogenated solids inlet to solids received in said hydrogenated solids inlet is in the range of 0.1:1 to 1:1.

23. The apparatus of claim 1 wherein said oxidation reactor has a feed inlet and an oxidant inlet that are separate from one another, wherein said feed inlet is configured for receipt of a liquid phase feed stream comprising an oxidizable compound, wherein said oxidant inlet is configured for receipt of a gas phase oxidant stream.

24. The apparatus of claim 23 wherein said oxidation reactor is configured to continuously receive said oxidizable compound at a rate of at least 5,000 kilograms per hour.

25. The apparatus of claim 23 wherein said oxidation reactor is configured to continuously receive said oxidizable compound at a rate of 10,000 to 80,000 kilograms per hour.

* * * * *